United States Patent
Wenzel

(10) Patent No.: US 11,219,430 B2
(45) Date of Patent: Jan. 11, 2022

(54) METHOD AND SYSTEM FOR AUTOMATICALLY PROVIDING ARTIFACT WARNINGS IN PULSED-WAVE DOPPLER IMAGING

(71) Applicant: GE Precision Healthcare LLC, Wauwatosa, WI (US)

(72) Inventor: Timo Wenzel, Seewalchen am Attersee (AT)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 260 days.

(21) Appl. No.: 16/661,240

(22) Filed: Oct. 23, 2019

(65) Prior Publication Data

US 2021/0121157 A1    Apr. 29, 2021

(51) Int. Cl.
*A61B 8/08* (2006.01)
*G01S 15/89* (2006.01)
*A61B 8/06* (2006.01)

(52) U.S. Cl.
CPC ............... *A61B 8/486* (2013.01); *A61B 8/06* (2013.01); *A61B 8/488* (2013.01); *G01S 15/895* (2013.01); *G01S 15/8988* (2013.01)

(58) Field of Classification Search
CPC ........... A61B 8/486; A61B 8/488; A61B 8/06; A61B 8/5269; A61B 8/085; A61B 8/52; G01S 15/8988; G01S 15/895; G01S 7/52066; G01S 7/52073
See application file for complete search history.

(56) References Cited

U.S. PATENT DOCUMENTS 6,322,509 B1    11/2001    Pan et al.
2014/0018680 A1    1/2014    Guracar

FOREIGN PATENT DOCUMENTS

JP    2005185731    7/2005

*Primary Examiner* — Bo Joseph Peng
(74) *Attorney, Agent, or Firm* — McAndrews, Held & Malloy, Ltd.; Jacob Groethe

(57) ABSTRACT

A system and method for automatically providing artifact warnings in Pulsed-Wave (PW) Doppler imaging is provided. The method includes acquiring, by an ultrasound system at a pulse repetition frequency (PRF), Pulsed-Wave (PW) Doppler signals from a selected gate position in a high PRF mode. The method includes determining, by a processor of the ultrasound system based on the PRF, a position of a virtual gate along a PW line in a B-mode image. The method includes presenting, at a display, the virtual gate at the determined position along the PW line in the B-mode image. The method includes analyzing, by the processor, B-mode image intensity values at the virtual gate in the B-mode image to determine whether the B-mode image intensity values exceed an intensity threshold. The method includes providing, by the at least one processor, a virtual gate warning when the B-mode image intensity values exceed the intensity threshold.

20 Claims, 8 Drawing Sheets

— PRIOR ART —

METHOD AND SYSTEM FOR AUTOMATICALLY PROVIDING ARTIFACT WARNINGS IN PULSED-WAVE DOPPLER IMAGING

FIELD

Certain embodiments relate to ultrasound imaging. More specifically, certain embodiments relate to a method and system for automatically providing artifact warnings in Pulsed-Wave (PW) Doppler imaging. In various embodiments, a virtual gate may be provided along a PW line in a B-mode image at positions corresponding to a selected pulse repetition frequency (PRF) to identify a location where ambiguities could arise. The system may provide a warning if a bright structure is identified at the position of the virtual gate such that the virtual gate may be moved by adjusting the PRF. In various embodiments, the system may analyze B-mode image intensity information along the PW line and identify sections of the PW line having an amplitude above a threshold to assist an operator in adjusting the PRF.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Pulsed-Wave (PW) Doppler signals are rich signals that describe the spectrum of tissue and fluid velocities in a small volume from which the signals are acquired. During a PW Doppler ultrasound examination of a patient, an operator may place a gate over a small region in a B-mode image, such as over a blood vessel. The velocity information of the blood vessel at the location of the gate may be presented in a spectrogram. FIG. 1 illustrates a B-mode image 10 and spectrogram 20, as known in the art. Referring to FIG. 1, the B-mode image 10 may include a PW line 14 and a selected gate 16 along the PW line 14. The gate 16 may be positioned at a location, such as over a blood vessel 12, to acquire velocity information of the blood vessel 12 at the gate location 16. The velocity information at the gate location 16 is presented in a spectrogram 20. The spectrogram 20 of FIG. 1 shows a constant flow 22 and background noise 24.

During a PW Doppler examination, transmit shots are repeated at the position of the PW line 14 and the received signals are used to generate the spectrogram 20. After transmitting a shot, the ultrasound system switches to receive mode. Each transmitted shot takes a certain amount of time, based on the speed of sound in a medium, until the wave front "hits" the scatterers at the gate 16 position. The return of the echoes takes the same amount of time. As an example, with a speed of sound of 1540 m/s and a gate depth of 10 cm, it takes 0.1 [m]/1540 [m/s]=65 [µs] times two after the transmit event (i.e. 130 µs) until the echoes from within the gate 16 are received. Accordingly, the next transmit event may start after 130 µs, which is equivalent to a pulse repetition frequency (PRF) of 7700 Hz (≈1/130 µs).

In practice, if a velocity of a flow is high, the PRF typically needs to be high to prevent aliasing. Accordingly, in a high PRF mode, subsequent transmit events begin prior to the echoes of the last transmit event being received. For example, if operating with a PRF of 10,000 Hz in a high PRF mode during a PW Doppler examination, a transmit event occurs every 100 µs. However, the return of the echoes from the gate depth takes 130 µs as noted in the example above. In other words, the ultrasound probe receives echoes 130 µs after a first transmit event, which is also 30 µs after the second transmit event. Echoes from the second transmit event are received after 130 µs, which is 30 µs after the third transmit event. The transmit and receive event timing continues in this pattern. However, a problem may occur if another vessel or highly reflective structure is at a depth that causes additional echoes to be received at the same time the echoes from the desired blood vessel are received. As an example, if a second vessel is located at a depth of 2.3 cm along the PW line 14 according to the above example, Doppler signals from the second vessel are received at the probe 30 µs after the second transmit event, which is the same time as the echoes are received from the first vessel 12 corresponding with the first transmit event.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically providing artifact warnings in Pulsed-Wave (PW) Doppler imaging, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
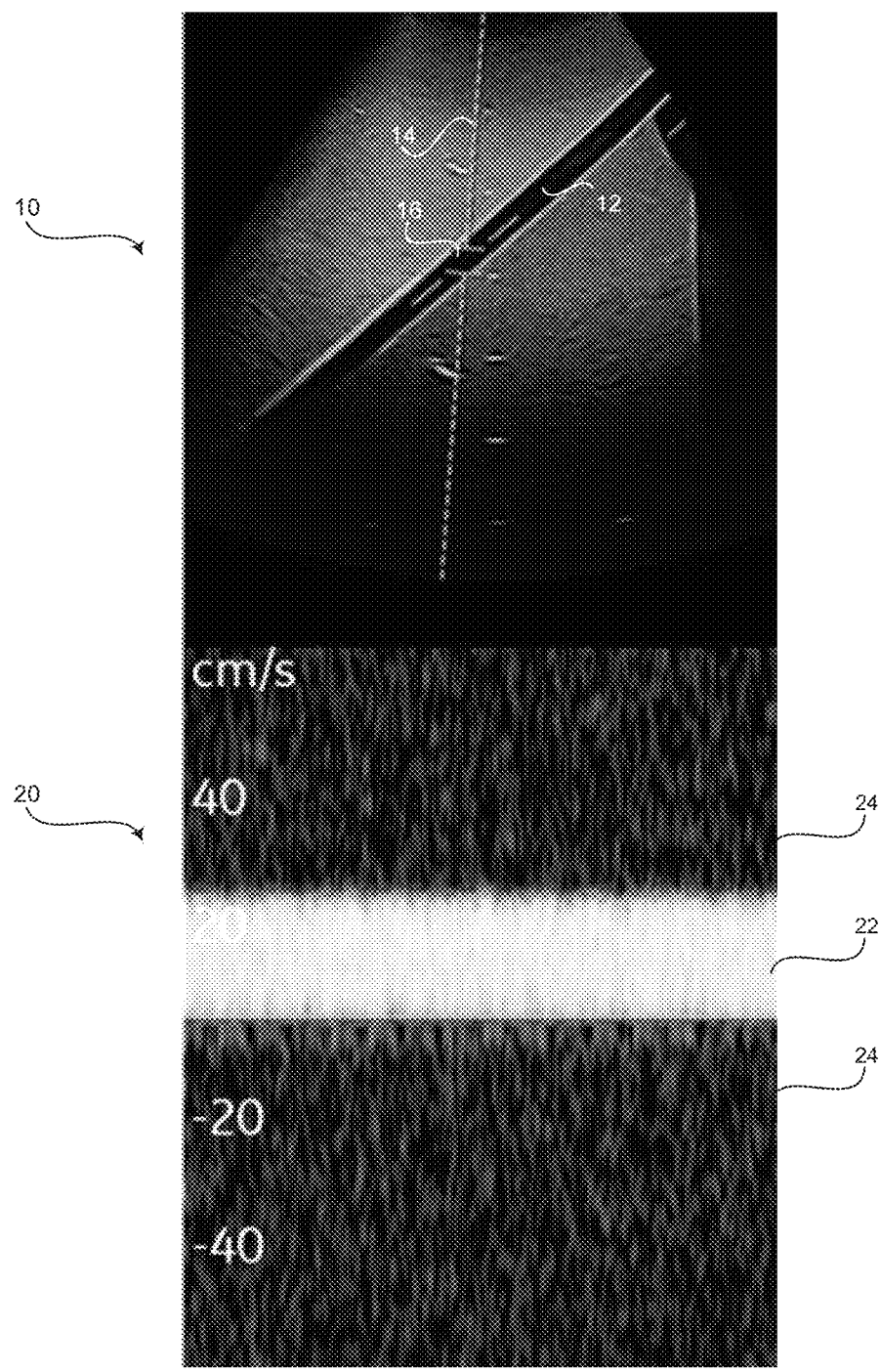
FIG. 1 illustrates a B-mode image and spectrogram, as known in the art.

Certain embodiments may be found in a method and system for automatically providing artifact warnings in Pulsed-Wave (PW) Doppler imaging. Various embodiments have the technical effect of providing visualization of ambiguities by providing a virtual gate along a PW line in a B-mode image at a position corresponding to a selected pulse repetition frequency (PRF). Moreover, certain embodiments have the technical effect of providing a warning if a highly reflective structure is identified at a position of the virtual gate such that the virtual gate may be moved by adjusting the PRF. Furthermore, aspects of the present disclosure have the technical effect of identifying sections of the PW line having B-mode image intensity amplitudes above a threshold to guide an operator in making PRF adjustments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 2.

Figure 2:
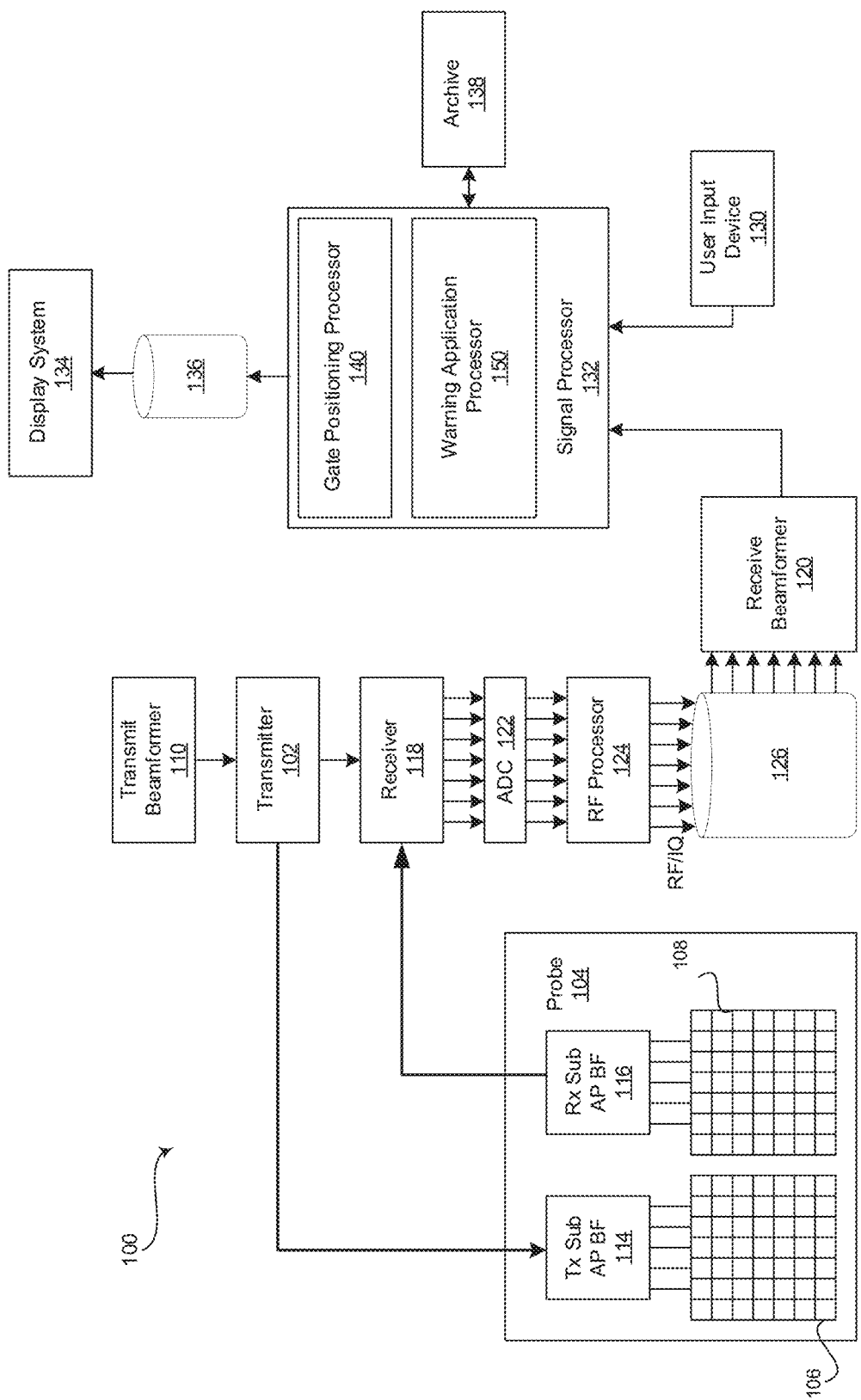
FIG. 2 is a block diagram of an exemplary ultrasound system that is operable to automatically provide artifact warnings in Pulsed-Wave (PW) Doppler imaging, in accordance with various embodiments.

FIG. 2 is a block diagram of an exemplary ultrasound system 100 that is operable to automatically provide artifact warnings in Pulsed-Wave (PW) Doppler imaging, in accordance with various embodiments. Referring to FIG. 2, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital.

The user input device 130 may be utilized to input patient data, scan parameters, settings, select protocols and/or templates, select an examination type, select gate locations, select acquisition and/or display processing parameters, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

In various embodiments, an examination type and/or desired gate locations may be selected at the onset of an imaging procedure in response to a directive received via the user input device 130. For example, an ultrasound operator may identify a PW Doppler examination and a gate location via the user input device 130. In an exemplary embodiment, acquisition parameters and/or display processing parameters may be identified and applied during an imaging procedure in response to a directive received via the user input device 130. For example, the ultrasound operator may select and/or adjust, via the user input device 130, a pulse repetition frequency for gates corresponding to blood flow anatomical structures. The acquisition parameters may be stored at archive 138 or any suitable data storage medium. As another example, the ultrasound operator may select, via the user input device 130, a set of display parameters for gates corresponding to blood flow anatomical structures. The display processing parameters may include scale, gain, brightness, contrast, and the like. The selected display processing parameters may be stored at archive 138 or any suitable data storage medium for retrieval and application to the acquired ultrasound data. In a representative embodiment, PW Doppler ultrasound data and/or a corresponding 2D image of a region of interest may be stored and/or retrieved in response to a directive received via the user input device 130.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform Doppler processing, compounding, motion tracking, and/or signal processing in time and frequency domains, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information. In the exemplary embodiment, the signal processor 132 may comprise a gate positioning processor 140 and a warning application processor 150.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a gate positioning processor 140 that comprises suitable logic, circuitry, interfaces and/or code that may be operable to position a gate on the B-mode image in response to a directive from the user input device 130. For example, after entering a PW Doppler mode, an operator may select, via the user input device 130, a gate position corresponding with the location on the B-mode image from which the operator desires to acquire the PW Doppler ultrasound data. The gate positioning processor 140 may be configured to present a visual representation of the gate on the B-mode image and may update the PW Doppler acquisition parameters to define the depth of the selected gate. In various embodiments, an operator may select and or adjust the PRF of the PW Doppler ultrasound image acquisition via the user input device 130. For example, an operator may increase the PRF based on the velocity of the flow at the selected gate location to visualize the velocity information in the spectrogram. The gate positioning processor 140 comprises suitable logic, circuitry, interfaces and/or code that may be operable to determine whether the selected PRF exceeds a threshold (i.e., high PRF mode). As an example, if the gate depth is 10 cm such that it takes 130 μs to receive the echoes from within the gate after the transmit event, the gate positioning processor 140 may determine whether the selected PRF is above 7700 Hz (≈1/130 μs). In an exemplary embodiment, the gate positioning processor 140 comprises suitable logic, circuitry, interfaces and/or code that may be operable to position a virtual gate on the B-mode image if the selected PRF exceeds the threshold such that the system is operating in the high PRF mode, which in the above example would correspond with a selected PRF exceeding a threshold of 7700 Hz. The gate positioning processor 140 may superimpose visual representations (e.g., icons) of the gate and/or virtual gate on the B-mode image for presentation at the display system 134. In certain embodiments, the visual representation of the virtual gate may provide an operator with information regarding potential ambiguities that may arise, such as a highly reflective structure (e.g., dense tissue or an additional blood vessel) located at the position of the virtual gate, such that the operator may adjust the PRF to avoid the highly reflective structure.

Figure 3:
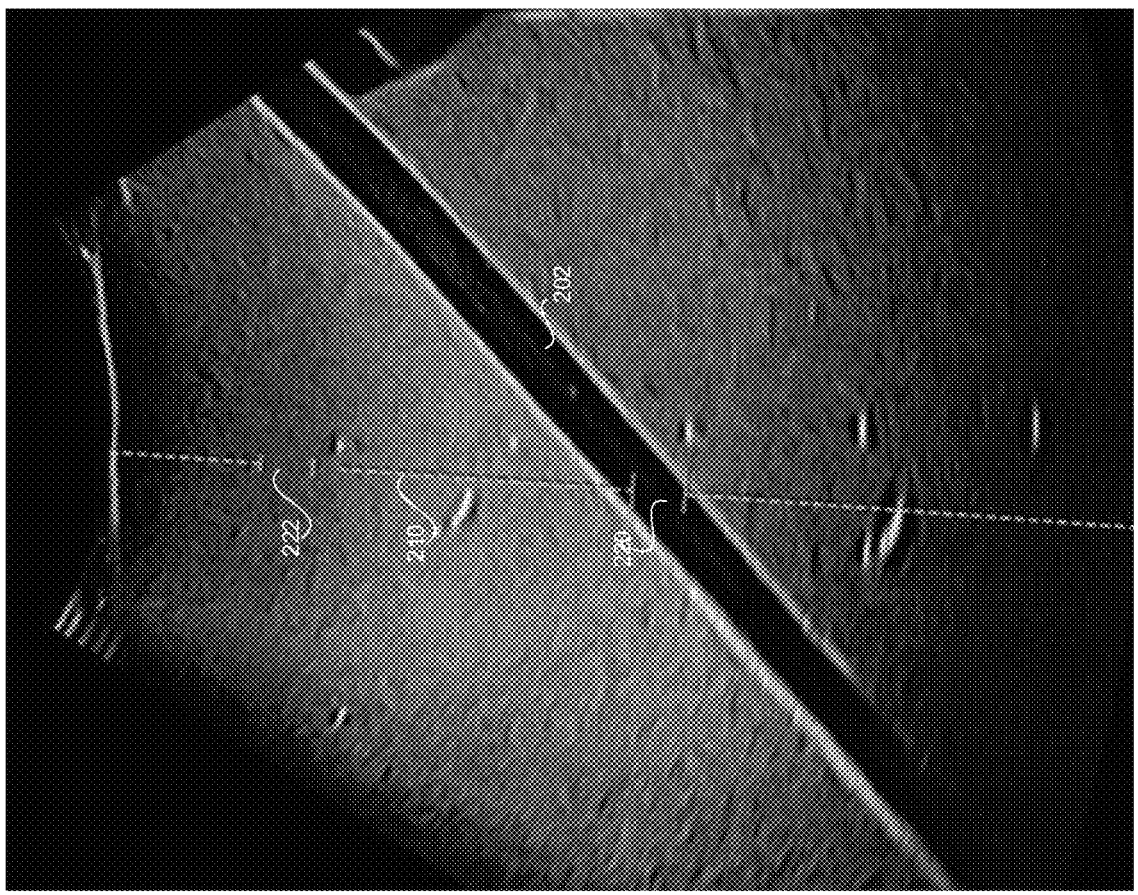
FIG. 3 illustrates an exemplary B-mode image having a selected gate location and a virtual gate location corresponding to a selected pulse repetition frequency (PRF), in accordance with various embodiments.
Figure 4:
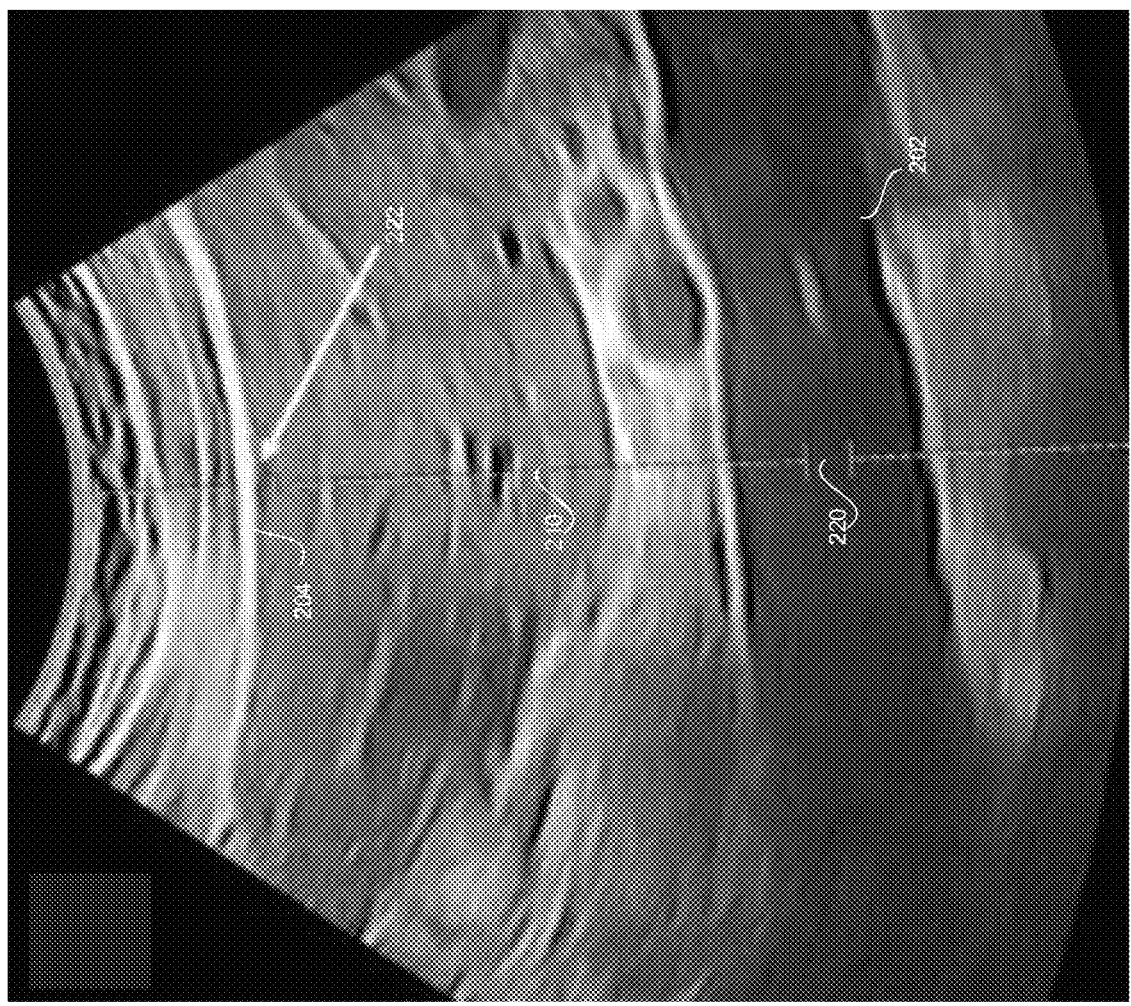
FIG. 4 illustrates an exemplary B-mode image having a selected gate location and a virtual gate location positioned, based on a selected PRF, at a bright structure, in accordance with various embodiments.

FIG. 3 illustrates an exemplary B-mode image 200 having a selected gate location 220 and a virtual gate location 222 corresponding to a selected pulse repetition frequency (PRF), in accordance with various embodiments. FIG. 4 illustrates an exemplary B-mode image 200 having a selected gate location 220 and a virtual gate location 222 positioned, based on a selected PRF, at a bright structure 204, in accordance with various embodiments. Referring to FIGS. 3 and 4, the B-mode images 200 may include a selected gate 220 along a PW line 210 positioned over a blood vessel 202 of interest. The B-mode images 200 may include a virtual gate 222 positioned by the gate positioning processor 140 based on the selected PRF. Referring to FIG. 4, the virtual gate 222 is located at a position of a bright structure 204. For purposes of the present disclosure, a bright structure (also referred to as a highly reflective structure) is defined as an imaged structure having an image intensity amplitude above a threshold image intensity value. In various embodiments, an operator may adjust the PRF via the user input device 130 to move the virtual gate 222 to a position that is not at a location of a bright structure 204.

Figure 5:
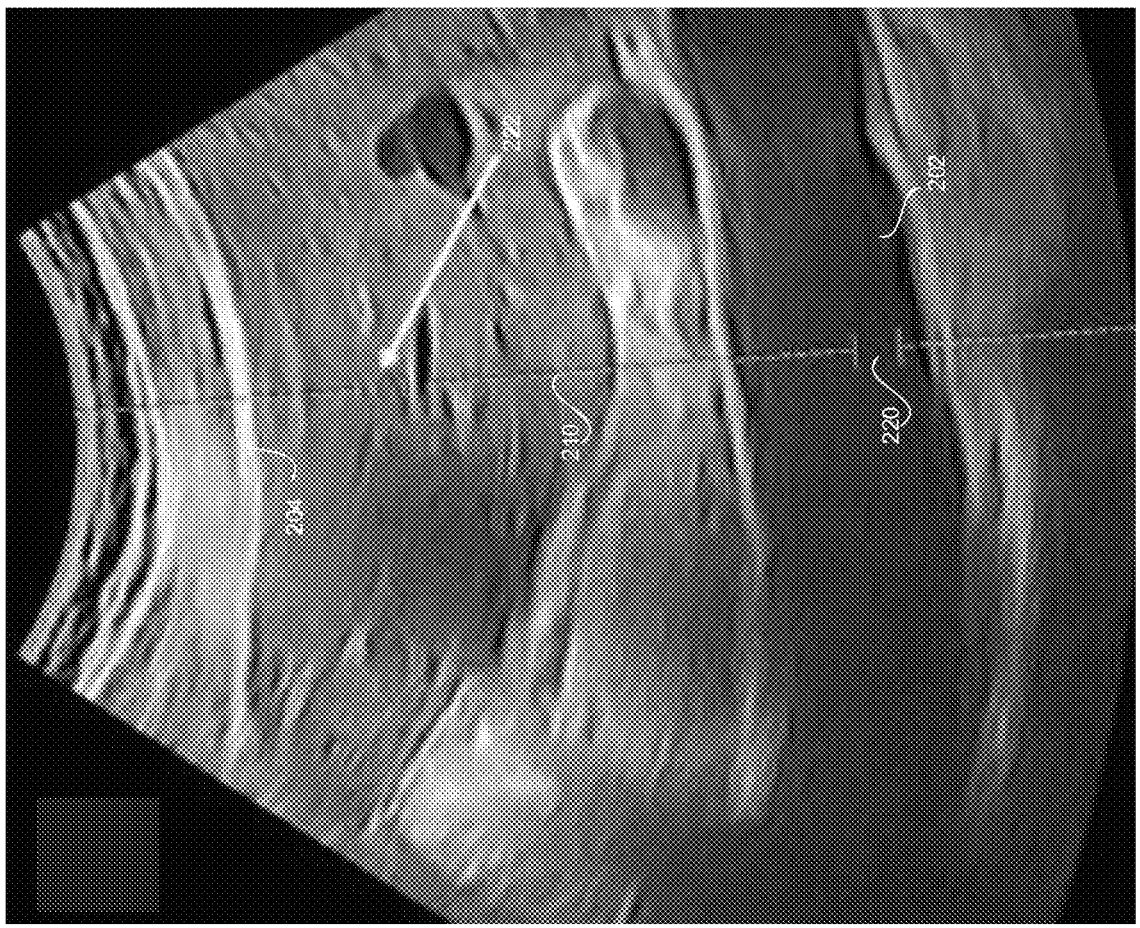
FIG. 5 illustrates an exemplary B-mode image having a selected gate location and a virtual gate location moved from the bright structure, as shown in FIG. 4, by adjusting the PRF, in accordance with various embodiments.

FIG. 5 illustrates an exemplary B-mode image 200 having a selected gate location 220 and a virtual gate location 222 moved from the bright structure 204, as shown in FIG. 4, by adjusting the PRF, in accordance with various embodiments. Referring to FIG. 5, the B-mode image 200 may include a selected gate 220 along a PW line 210 positioned over a blood vessel 202 of interest. The B-mode image 200 may include a virtual gate 222 moved by the gate positioning processor 140 based on the adjusted PRF. The adjustment of the PRF to move the virtual gate 222 to a position that does not correspond with a bright structure 204 provides enhanced visualization of the spectrogram by reducing or eliminating artifacts that may have been present due to the bright structure 204.

Referring again to FIG. 2, the signal processor 132 may include a warning application processor 150 that comprises suitable logic, circuitry, interfaces and/or code that may be operable to analyze B-mode image intensity values at the virtual gate 222 to determine whether the values exceed an intensity threshold. For example, a pre-defined and/or user selected image intensity threshold may correspond with image intensity values of structures expected to provide artifacts in the PW Doppler ultrasound image data. As an example, dense tissue 204 between an ultrasound probe 104 and the selected gate 220 may provide echoes in response to a second ultrasound transmit event that can be received at the probe 104 at a same time echoes from structure at the selected gate 220 in response to a first ultrasound transmit event are received if the virtual gate 222 is positioned at the location of the dense tissue 204. The warning application processor 150 comprises suitable logic, circuitry, interfaces and/or code that may be operable to provide visual, audio, and/or physical feedback to warn an operator that the virtual gate 222 is positioned at a location of a bright structure 204 if the warning application processor 150 determines that the intensity values at the virtual gate 222 exceed the intensity threshold. For example, the warning application processor 150 may present text, shapes, colorized pixels, and/or any suitable visual indicator identifying the virtual gate 222 being positioned at a location of a bright structure 204. As another example, the warning application processor 150 may additionally and/or alternatively provide an audio tone, beep, warning message, and/or any suitable audio output to warn an operator that the virtual gate 222 is positioned at a location of a bright structure 204. Additionally and/or alternatively, the warning application processor 150 may provide a physical warning, such as vibrations at the ultrasound probe 104, to alert an operator that the virtual gate 222 is positioned at a location of a bright structure 204.

In various embodiments, the warning application processor 150 comprises suitable logic, circuitry, interfaces and/or code that may be operable to analyze B-mode image intensity values along the PW line 210 to determine whether and/or where the values exceed an intensity threshold. The warning application processor 150 may present warnings at the display system 134 identifying locations along the PW line 210 that are associated with bright structures 204. The operator may consult the visual feedback to provide PRF adjustments to move the virtual gate 222 to a location that is not associated with a bright structure 204. The PW line warnings may be provided additionally and/or as an alternative to the virtual gate warnings described above.

Figure 6:
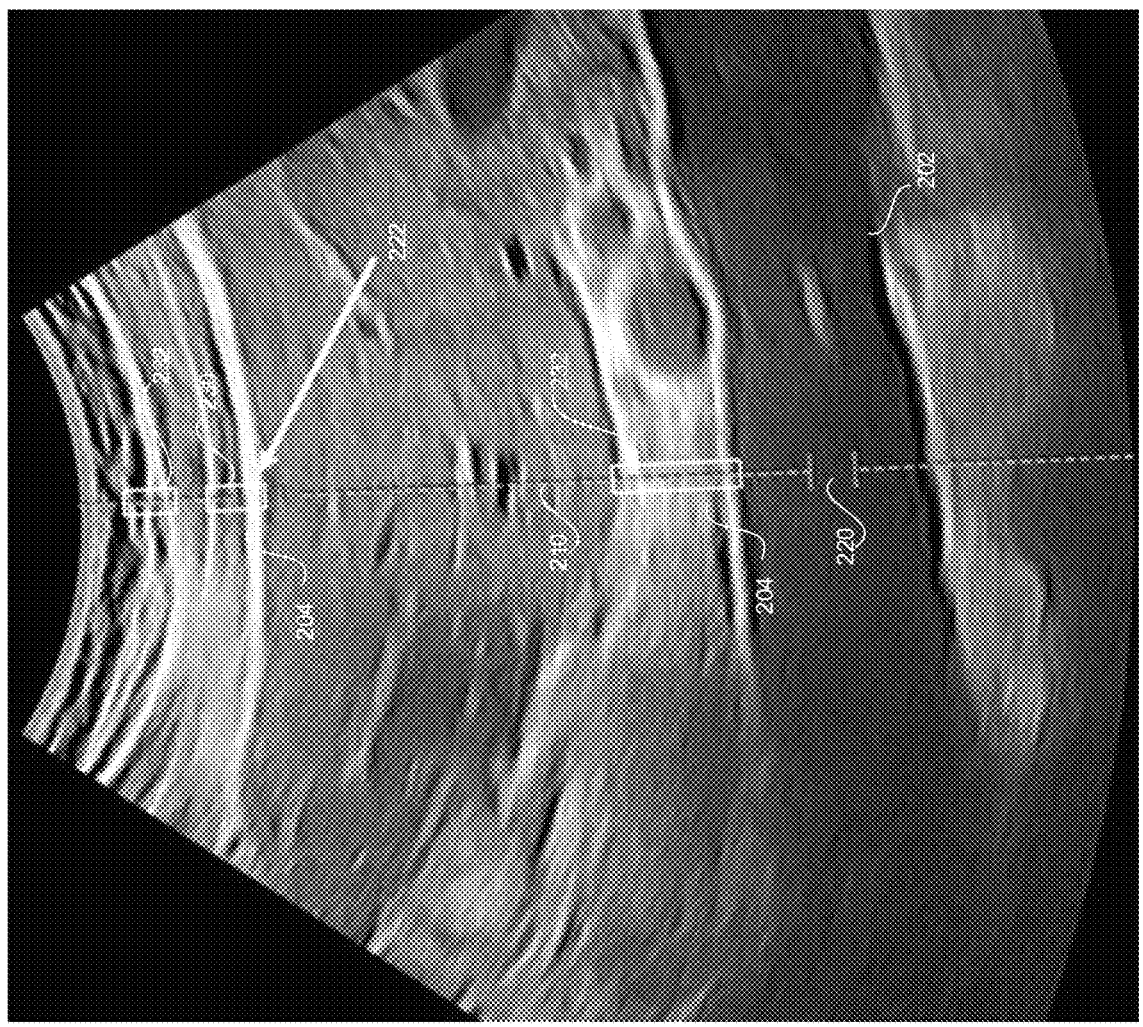
FIG. 6 illustrates an exemplary B-mode image having a selected gate location, a virtual gate location, and warnings provided along a PW line, in accordance with various embodiments.

FIG. 6 illustrates an exemplary B-mode image 200 having a selected gate location 220, a virtual gate location 222, and warnings 230, 232 provided along a PW line 210, in accordance with various embodiments. Referring to FIG. 6, the B-mode image 200 may include a selected gate 220 along a PW line 210 positioned over a blood vessel 202 of interest. The B-mode image 200 may include a virtual gate 222 positioned by the gate positioning processor 140 based on the selected PRF. The B-mode image 200 may include bright structures 204 that could provide artifacts in PW Doppler ultrasound image data if the virtual gate 222 is positioned at the same location as one or more of the bright structures 204. The warning application processor 150 may provide a virtual gate warning 230 at the display system 134, as shown in FIG. 6, when the virtual gate 222 is positioned at the location of a bright structure 204. The warning application processor 150 may provide PW line warnings 232 at locations along the PW line 210 where bright structures 204 are present. The virtual gate warning 230 alerts an operator that the PRF should be adjusted to avoid artifacts in the PW Doppler ultrasound image data. The PW line warnings 232 provide feedback to the operator regarding other bright structure 204 locations so that the operator may adjust the PRF to avoid the bright structure 204 locations.

Figure 7:
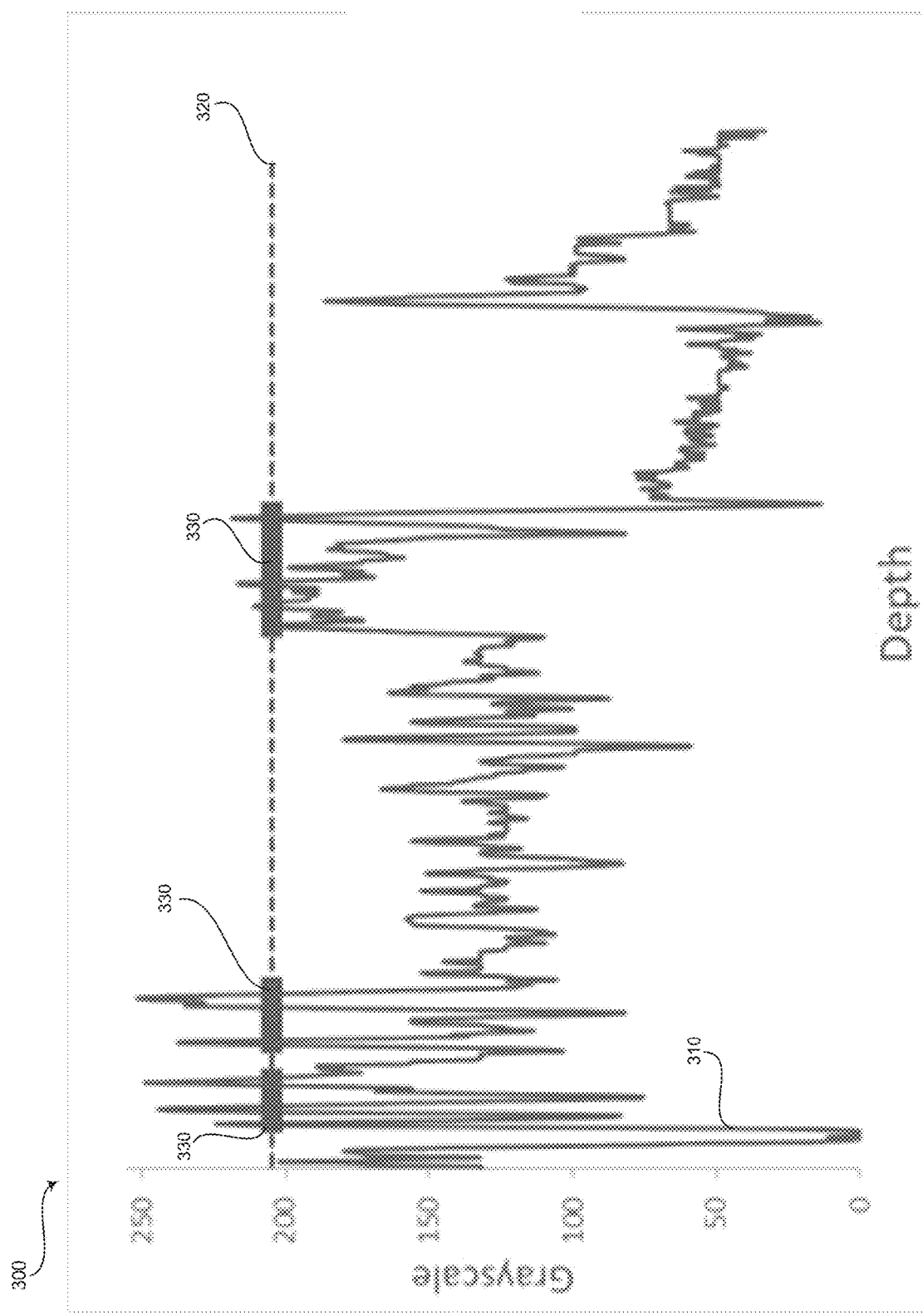
FIG. 7 illustrates an exemplary graph of B-mode image intensity information along a PW line of a B-mode image with respect to an intensity threshold, in accordance with various embodiments.

FIG. 7 illustrates an exemplary graph 300 of B-mode image intensity information along a PW line 210 of a B-mode image 200 with respect to an intensity threshold, in accordance with various embodiments. Referring to FIG. 7, the graph includes image intensity values (x-axis) at various depths (y-axis) of the B-mode image data 310 along the PW line 210. The graph 300 includes a B-mode ultrasound image intensity threshold 320 and warning locations 330 to provide virtual gate 230 and/or PW line warnings 232.

Referring again to FIG. 2, the display system 134 may be any device capable of communicating visual information to a user. For example, a display system 134 may include a liquid crystal display, a light emitting diode display, and/or any suitable display or displays. The display system 134 can be operable to present ultrasound images and/or any suitable information. For example, the ultrasound images presented at the display system 134 may include B-mode images 200, spectrograms, PW lines 210, selected gates 220, virtual gates 222, warnings 230, 232, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound image data, selected gate positioning instructions, PRF threshold information and instructions, virtual gate positioning instructions, image intensity threshold information and instructions, warning instructions, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Figure 8:
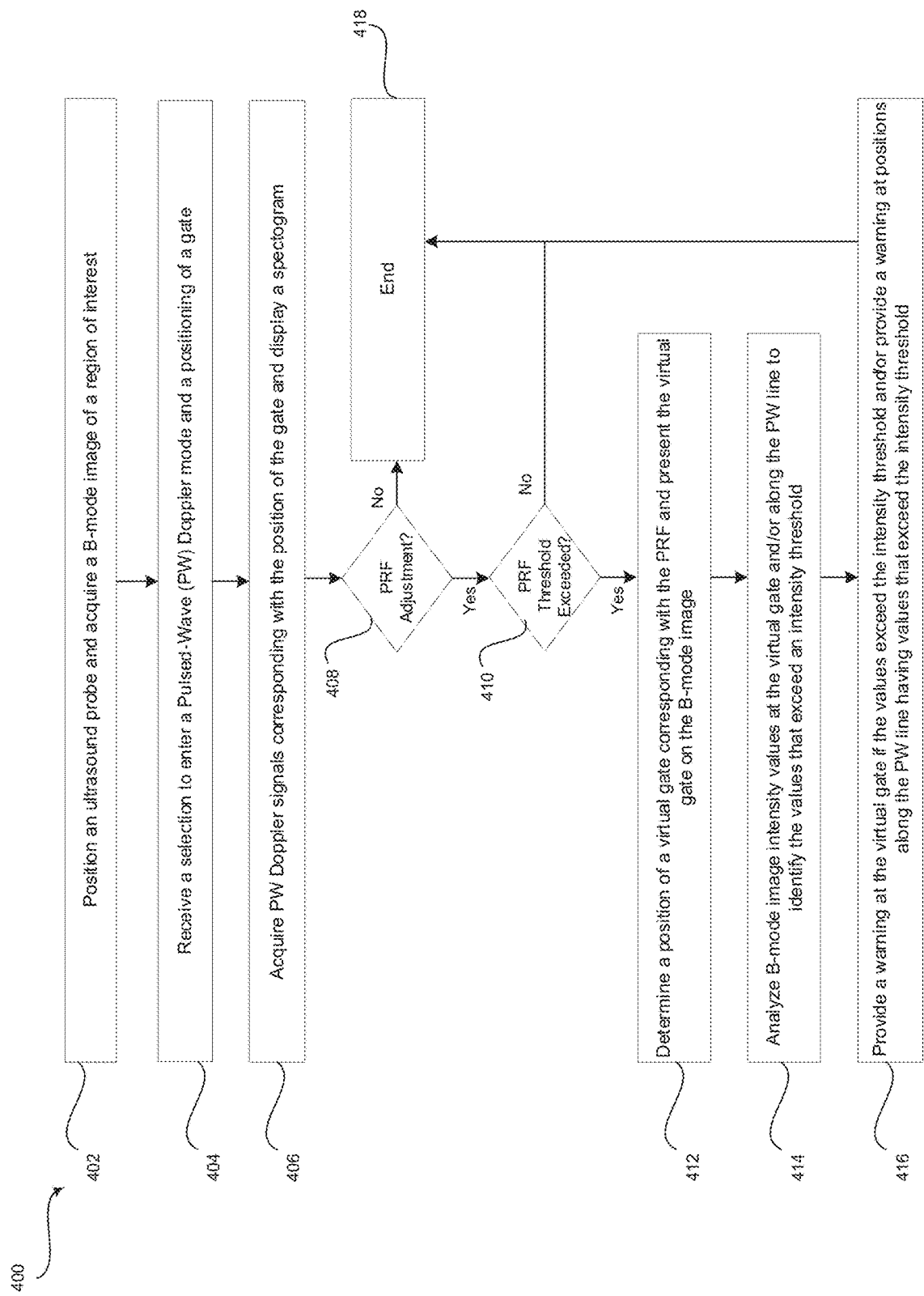
FIG. 8 is a flow chart illustrating exemplary steps that may be utilized for automatically providing artifact warnings in PW Doppler imaging, in accordance with exemplary embodiments.

FIG. 8 is a flow chart 400 illustrating exemplary steps 402-418 that may be utilized for automatically providing artifact warnings 230, 232 in PW Doppler imaging, in accordance with exemplary embodiments. Referring to FIG. 8, there is shown a flow chart 400 comprising exemplary steps 402 through 418. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, a probe 104 of an ultrasound system 100 may be positioned to acquire a B-mode image 200 of a region of interest. For example, the ultrasound system 100 may acquire the B-mode image 200 with an ultrasound probe 104 positioned over a region of interest, such as venous blood flow, arterial blood flow, mitral inflow, muscle tissue, and/or any suitable anatomical structures.

At step 404, a signal processor 132 of the ultrasound system 100 may receive a selection to enter a PW Doppler mode and a positioning of a gate 220. For example, the signal processor 132 may receive a selection to enter a PW Doppler mode from a user input device 130, such as the depression of a button, a selection on a touchscreen, or any suitable user input. A gate positioning processor 140 of the signal processor 132 may receive a gate selection, via the user input device 130, at a location on the B-mode image 200 at which velocity information is desired. The gate positioning processor 140 may be configured to superimpose a gate 220 at the selected location on the B-mode image 200.

At step 406, the ultrasound system 100 may acquire PW Doppler signals corresponding with the position of the gate 220 and display a spectrogram. For example, the ultrasound probe may acquire the PW Doppler signals corresponding with the position of the gate selected at step 404. The ultrasound system 100 may process the PW Doppler signals to generate the spectrogram, which may be presented at a display system 134.

At step 408, the signal processor 132 may determine whether a PRF adjustment is received. For example, an operator may increase a PRF to view velocity information in the spectrogram of higher velocity flows that may not be viewable at the default or initial PRF setting. The process 400 may continue to step 410 if a PRF adjustment is received by the signal processor 132 via the user input device 130. The process 400 may end at step 418 if no PRF adjustment is received at step 408.

At step 410, the signal processor 132 determines whether the adjusted PRF exceeds a PRF threshold. For example, the gate positioning processor 140 of the signal processor 132 may compare a PRF adjustment received at step 408 to a PRF threshold to determine whether the system is operating in a high PRF mode, which is defined as an operating mode where a time between transmit events is less than a time it takes to receive echoes from the structure at the selected gate location. The process 400 may end at step 418 if the PRF adjustment at step 408 does not result in the system 100 entering a high PRF mode. The process 400 may continue to step 412 if the PRF adjustment at step 408 results in the system 100 entering a high PRF mode.

At step 412, the signal processor 132 may determine a position of a virtual gate 222 corresponding with the PRF and present the virtual gate 222 on the B-mode image 200. For example, the gate positioning processor 150 of the signal processor 132 may determine a depth, based on the PRF selected at step 408, that may provide echoes from a second transmit event to the ultrasound probe 104 at a same time that echoes from a first transmit event corresponding with the selected gate 220 are received by the ultrasound probe 104. The gate positioning processor 150 may present a visual indicator of the virtual gate 222 overlaid on the B-mode image 200 along the PW line 210 at the determined depth.

At step 414, the signal processor 132 may analyze B-mode image intensity values at the virtual gate 222 and/or along the PW line 210 to identify the values that exceed an intensity threshold. For example, a warning application processor 150 of the signal processor 132 may be configured to determine whether the intensity values of B-mode image pixels at the virtual gate 222 and/or along the PW line 210 exceed an intensity threshold that corresponds to bright structure 204 that may provide artifacts in the PW Doppler ultrasound image data.

At step 416, the signal processor 132 may provide a warning 230 at the virtual gate 222 if the intensity values exceed the intensity threshold and/or may provide a warning 230, 232 at positions along the PW line 210 having intensity values that exceed the intensity threshold. For example, the warning application processor 150 of the signal processor 132 may present text, shapes, colorized pixels, and/or any suitable visual indicator 230 at the display system 134 identifying the virtual gate 222 being positioned at a location of a bright structure 204. As another example, the warning application processor 150 may present warnings 232 at the display system 134 identifying locations along the PW line 210 that are associated with bright structures 204. The operator may consult the visual feedback to provide PRF adjustments to move the virtual gate 222 to a location that is not associated with a bright structure 204. The process 400 may return to step 408 if additional PRF adjustments are made, for example, if the virtual gate 222 is positioned at a bright structure 204. The process 400 may end at step 418 when the ultrasound procedure is finished.

Aspects of the present disclosure provide a method 400 and system 100 for automatically providing artifact warnings 230, 232 in Pulsed-Wave (PW) Doppler imaging. In accordance with various embodiments, the method 400 may comprise acquiring 406, by an ultrasound system 100 at a pulse repetition frequency (PRF), Pulsed-Wave (PW) Doppler signals from a selected gate position 220 in a high PRF mode. The high PRF mode occurs when a first time between a first transmit event and a second transmit event is less than a second time between the first transmit event and a first receive event corresponding with the PW Doppler signals acquired from the selected gate position 220 in response to the first transmit event. The method 400 may comprise determining 412, by at least one processor 132, 140 of the ultrasound system 100 based on the PRF, a position of a virtual gate 222 along a PW line 210 in a B-mode image 200. The method 400 may comprise presenting 412, at a display system 134, the virtual gate 222 at the determined position along the PW line 210 in the B-mode image 200. The method 400 may comprise analyzing 414, by the at least one processor 132, 150, B-mode image intensity values 310 at the virtual gate 222 in the B-mode image 200 to determine whether the B-mode image intensity values 310 exceed an intensity threshold 320. The method 400 may comprise providing 416, by the at least one processor 132, 150, a virtual gate warning 230 when the B-mode image intensity values 310 exceed the intensity threshold 320.

In a representative embodiment, the method 400 may comprise acquiring 402, by the ultrasound system 100, the B-mode image 200. The method 400 may comprise receiving 404, by the at least one processor 132, a selection to enter a PW Doppler mode from a user input device 130. The method 400 may comprise receiving 404, by the at least one processor 132, 140, the selected gate position 220 from the user input device 130. The method 400 may comprise presenting 404, at the display system 132, the selected gate position 220 in the B-mode image 200. In an exemplary embodiment, the method 400 may comprise receiving 408, by the at least one processor 132, 140, an adjustment to the PRF from a user input device 130. The method 400 may comprise determining 410, by the at least one processor 132, 140, whether the adjustment to the PRF corresponds with the high PRF mode. In various embodiments, the method 400 may comprise analyzing 414, by the at least one processor 132, 150, the B-mode image intensity values 310 along the PW line 210 in the B-mode image to identify the B-mode image intensity values 310 along the PW line 210 that exceed the intensity threshold 320. The method 400 may comprise presenting 416, at the display system 134, a PW line warning 232 at positions along the PW line 210 having the B-mode image intensity values 310 that exceed the intensity threshold 320. In certain embodiments, the method 400 may comprise receiving 408, by the at least one processor 132, 140, an adjusted PRF from a user input device 130 in response to the virtual gate warning 230 and the PW line warning 232. In a representative embodiment, the PW line warning 232 is a visual indicator comprising text, at least one shape 232, and/or colorized pixels. In an exemplary embodiment, the method 400 comprises receiving 408, by the at least one processor 132, 140, an adjusted PRF from a user input device 130 in response to the virtual gate warning 230. In certain embodiments, the virtual gate warning 230 is a visual warning 230, an audio warning, and/or a physical warning.

Various embodiments provide a system 100 for automatically providing artifact warnings 230, 232 in Pulsed-Wave (PW) Doppler imaging. The system 100 may comprise an ultrasound system 100, at least one processor 132, 140, 150, and a display system 134. The ultrasound system 100 may be configured to acquire Pulsed-Wave (PW) Doppler signals at a pulse repetition frequency (PRF) from a selected gate position 220 in a high PRF mode. The high PRF mode may occur when a first time between a first transmit event and a second transmit event is less than a second time between the first transmit event and a first receive event corresponding with the PW Doppler signals acquired from the selected gate position 220 in response to the first transmit event. The at least one processor 132, 140 may be configured to determine a position of a virtual gate 222 along a PW line 210 in a B-mode image 200 based on the PRF. The at least one processor 132, 150 may be configured to analyze B-mode image intensity values 310 at the virtual gate 222 in the B-mode image 200 to determine whether the B-mode image intensity values 310 exceed an intensity threshold 320. The at least one processor 132, 150 may be configured to provide a virtual gate warning 230 when the B-mode image intensity values 310 exceed the intensity threshold 320. The display system 134 may be configured to present the virtual gate 222 at the determined position along the PW line 210 in the B-mode image 200.

In an exemplary embodiment, the ultrasound system 100 may be configured to acquire the B-mode image 200. The at least one processor 132 may be configured to receive a selection to enter a PW Doppler mode from a user input device 130. The at least one processor 132, 140 may be configured to receive the selected gate position 220 from the user input device 130. The display system 134 may be configured to present the selected gate position 220 in the B-mode image 210. In certain embodiments, the at least one processor 132, 140 may be configured to receive an adjustment to the PRF from a user input device 130. The at least one processor 132, 140 may be configured to determine whether the adjustment to the PRF corresponds with the high PRF mode. In various embodiment, the at least one processor 132, 150 may be configured to analyze the B-mode image intensity values 310 along the PW line 210 in the B-mode image 200 to identify the B-mode image intensity values 310 along the PW line 210 that exceed the intensity threshold 320. The at least one processor 132, 150 may be configured to present, at the display system 134, a PW line warning 232 at positions along the PW line 210 having the B-mode image intensity values 310 that exceed the intensity threshold 320. In a representative embodiment, the at least one processor 132, 140 may be configured to receive an adjusted PRF from the user input device 130 in response to the virtual gate warning 230 and the PW line warning 232. In an exemplary embodiment, the at least one processor 132, 140 is configured to receive an adjusted PRF from a user input device 130 in response to the virtual gate warning 230. In various embodiments, the virtual gate warning 230 may be a visual warning 230, an audio warning, and/or a physical warning.

Certain embodiments provide a non-transitory computer readable medium having stored thereon, a computer program having at least one code section. The at least one code section is executable by a machine for causing the machine to perform steps 400. The steps 400 may comprise receiving 406 Pulsed-Wave (PW) Doppler signals acquired at a pulse repetition frequency (PRF) from a selected gate position 220 in a high PRF mode. The high PRF mode occurs when a first time between a first transmit event and a second transmit event is less than a second time between the first transmit event and a first receive event corresponding with the PW Doppler signals acquired from the selected gate position 220 in response to the first transmit event. The steps 400 may comprise determining 412 a position of a virtual gate 222 along a PW line 210 in a B-mode image 200 based on the PRF. The steps 400 may comprise presenting 412 the virtual gate 222 at the determined position along the PW line 210 in the B-mode image 200 at a display system 134. The steps 400 may comprise analyzing 414 B-mode image intensity values 310 at the virtual gate 222 in the B-mode image 210 to determine whether the B-mode image intensity values 310 exceed an intensity threshold 320. The steps 400 may comprise providing 416 a virtual gate warning 230 when the B-mode image intensity values 310 exceed the intensity threshold 320.

In various embodiments, the steps 400 may comprise receiving 402 the B-mode image 200. The steps 400 may comprise receiving 404 a selection to enter a PW Doppler mode. The steps 400 may comprise receiving 404 the selected gate position 220. The steps 400 may comprise presenting 404 the selected gate position 220 in the B-mode image 200 at the display system 134. In an exemplary embodiment, the steps 400 may comprise analyzing 414 the B-mode image intensity values 310 along the PW line 210 in the B-mode image 200 to identify the B-mode image intensity values 310 along the PW line 210 that exceed the intensity threshold 320. The steps 400 may comprise presenting 416 a PW line warning 232 at positions along the PW line 210 having the B-mode image intensity values 310 that exceed the intensity threshold 320 at the display system 134. In a representative embodiment, the steps 400 may comprise receiving 408 an adjusted PRF in response to the virtual gate warning 230 and the PW line warning 232. In certain embodiments, the steps 400 may comprise receiving 408 an adjusted PRF in response to the virtual gate warning 230.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically providing artifact warnings in Pulsed-Wave (PW) Doppler imaging.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:
1. A method comprising:
   acquiring, by an ultrasound system at a pulse repetition frequency (PRF), Pulsed-Wave (PW) Doppler signals from a selected gate position in a high PRF mode, wherein a first time between a first transmit event and a second transmit event is less than a second time between the first transmit event and a first receive event corresponding with the PW Doppler signals acquired from the selected gate position in response to the first transmit event;

determining, by at least one processor of the ultrasound system based on the PRF, a position of a virtual gate along a PW line in a B-mode image;
presenting, at a display system, the virtual gate at the determined position along the PW line in the B-mode image;
analyzing, by the at least one processor, B-mode image intensity values at the virtual gate in the B-mode image to determine whether the B-mode image intensity values exceed an intensity threshold; and
providing, by the at least one processor, a virtual gate warning when the B-mode image intensity values exceed the intensity threshold.

2. The method of claim 1, comprising:
acquiring, by the ultrasound system, the B-mode image;
receiving, by the at least one processor, a selection to enter a PW Doppler mode from a user input device;
receiving, by the at least one processor, the selected gate position from the user input device; and
presenting, at the display system, the selected gate position in the B-mode image.

3. The method of claim 1, comprising:
receiving, by the at least one processor, an adjustment to the PRF from a user input device; and
determining, by the at least one processor, whether the adjustment to the PRF corresponds with the high PRF mode.

4. The method of claim 1, comprising:
analyzing, by the at least one processor, the B-mode image intensity values along the PW line in the B-mode image to identify the B-mode image intensity values along the PW line that exceed the intensity threshold; and
presenting, at the display system, a PW line warning at positions along the PW line having the B-mode image intensity values that exceed the intensity threshold.

5. The method of claim 4, comprising receiving, by the at least one processor, an adjusted PRF from a user input device in response to the virtual gate warning and the PW line warning.

6. The method of claim 4, wherein the PW line warning is a visual indicator comprising:
text,
at least one shape, and/or
colorized pixels.

7. The method of claim 1, comprising receiving, by the at least one processor, an adjusted PRF from a user input device in response to the virtual gate warning.

8. The method of claim 1, wherein the virtual gate warning is:
a visual warning,
an audio warning, and/or
a physical warning.

9. A system comprising:
an ultrasound system configured to acquire Pulsed-Wave (PW) Doppler signals at a pulse repetition frequency (PRF) from a selected gate position in a high PRF mode, wherein a first time between a first transmit event and a second transmit event is less than a second time between the first transmit event and a first receive event corresponding with the PW Doppler signals acquired from the selected gate position in response to the first transmit event;
at least one processor configured to:
determine a position of a virtual gate along a PW line in a B-mode image based on the PRF;
analyze B-mode image intensity values at the virtual gate in the B-mode image to determine whether the B-mode image intensity values exceed an intensity threshold; and
provide a virtual gate warning when the B-mode image intensity values exceed the intensity threshold; and
a display system configured to present the virtual gate at the determined position along the PW line in the B-mode image.

10. The system of claim 9, wherein:
the ultrasound system is configured to acquire the B-mode image;
the at least one processor is configured to receive:
a selection to enter a PW Doppler mode from a user input device, and
the selected gate position from the user input device; and
the display system is configured to present the selected gate position in the B-mode image.

11. The system of claim 9, wherein the at least one processor is configured to:
receive an adjustment to the PRF from a user input device; and
determine whether the adjustment to the PRF corresponds with the high PRF mode.

12. The system of claim 9, wherein the at least one processor is configured to:
analyze the B-mode image intensity values along the PW line in the B-mode image to identify the B-mode image intensity values along the PW line that exceed the intensity threshold, and
present, at the display system, a PW line warning at positions along the PW line having the B-mode image intensity values that exceed the intensity threshold.

13. The system of claim 12, wherein the at least one processor is configured to receive an adjusted PRF from the user input device in response to the virtual gate warning and the PW line warning.

14. The system of claim 9, wherein the at least one processor is configured to receive an adjusted PRF from a user input device in response to the virtual gate warning.

15. The system of claim 9, wherein the virtual gate warning is:
a visual warning,
an audio warning, and/or
a physical warning.

16. A non-transitory computer readable medium having stored thereon, a computer program having at least one code section, the at least one code section being executable by a machine for causing the machine to perform steps comprising:
receiving Pulsed-Wave (PW) Doppler signals acquired at a pulse repetition frequency (PRF) from a selected gate position in a high PRF mode, wherein a first time between a first transmit event and a second transmit event is less than a second time between the first transmit event and a first receive event corresponding with the PW Doppler signals acquired from the selected gate position in response to the first transmit event;
determining a position of a virtual gate along a PW line in a B-mode image based on the PRF;
presenting the virtual gate at the determined position along the PW line in the B-mode image at a display system;

analyzing B-mode image intensity values at the virtual gate in the B-mode image to determine whether the B-mode image intensity values exceed an intensity threshold; and providing a virtual gate warning when the B-mode image intensity values exceed the intensity threshold.

17. The non-transitory computer readable medium of claim 16, comprising:

receiving the B-mode image;

receiving a selection to enter a PW Doppler mode;

receiving the selected gate position; and presenting the selected gate position in the B-mode image at the display system.

18. The non-transitory computer readable medium of claim 16, comprising:

analyzing the B-mode image intensity values along the PW line in the B-mode image to identify the B-mode image intensity values along the PW line that exceed the intensity threshold; and presenting a PW line warning at positions along the PW line having the B-mode image intensity values that exceed the intensity threshold at the display system.

19. The non-transitory computer readable medium of claim 18, comprising receiving an adjusted PRF in response to the virtual gate warning and the PW line warning.

20. The non-transitory computer readable medium of claim 16, comprising receiving an adjusted PRF in response to the virtual gate warning.

* * * * *